(12) United States Patent
Yuan et al.

(10) Patent No.: US 8,772,488 B2
(45) Date of Patent: Jul. 8, 2014

(54) CRYSTALS OF PRASUGREL HYDROBROMATE (75) Inventors: Zhedong Yuan, Shanghai (CN); Xingdong Cheng, Shanghai (CN); Yulei Yang, Shanghai (CN); Ling Tong, Shanghai (CN); Xiong Yu, Shanghai (CN); Laifang Zhang, Nanjing (CN); Wenliang Zhou, Jiangsu (CN)

(73) Assignees: Shanghai Institute of Pharmaceutical Industry, Shanghai (CN); Chia Tai Tianqing Pharmaceutical Group Co., Ltd, Jiangsu Province (CN)

( * ) Notice: Subject to any disclaimer, the term of this patent is extended or adjusted under 35 U.S.C. 154(b) by 181 days.

(21) Appl. No.: 13/262,093

(22) PCT Filed: Mar. 31, 2010

(86) PCT No.: PCT/CN2010/071464
§ 371 (c)(1),
(2), (4) Date: Dec. 19, 2011

(87) PCT Pub. No.: WO2010/111951
PCT Pub. Date: Oct. 7, 2010

(65) Prior Publication Data
US 2012/0095035 A1    Apr. 19, 2012

(30) Foreign Application Priority Data

Mar. 31, 2009    (CN) .......................... 2009 1 0030050

(51) Int. Cl.
*A61K 31/44*    (2006.01)
*C07D 471/02*    (2006.01)
*A61K 31/4365*    (2006.01)
*C07D 495/04*    (2006.01)

(52) U.S. Cl.
CPC .......... *A61K 31/4365* (2013.01); *C07D 495/04* (2013.01)
USPC .......................................... 546/113; 514/301

(58) Field of Classification Search
None
See application file for complete search history.

(56) References Cited

FOREIGN PATENT DOCUMENTS

| CN | 101255169 | 9/2008 |
| CN | 200910030050.3 | 6/2010 |
| IN | 1596/MUM/2009 | 7/2009 |
| WO | 2008/000418 | 1/2008 |
| WO | WO2008000418 | 1/2008 |
| WO | 2011/004392 | 1/2011 |

OTHER PUBLICATIONS

Communication pursuant to Rule 114(2) EPC issued by the European Patent Office on Sep. 27, 2012 in connection with European Patent Application No. 10758053.2.

*Primary Examiner* — Heidi Reese
(74) *Attorney, Agent, or Firm* — Cesari and McKenna, LLP (57) ABSTRACT The present application discloses crystals of 2-acetoxy-5-(α-cyclopropylcarbonyl-2-fluorobenzyl)-4,5,6,7-tetrahydrothieno[3,2-c]pyridine hydrobromate, crystal compositions and pharmaceutical compositions comprising them and their use. The crystals of prasugrel hydrobromate of the present application possess excellent stability and solubility.

11 Claims, 8 Drawing Sheets

FIG 1a

Peak Search Report (46 Peaks, Max P/N = 48.5)
PEAK: 35-pts/Parabolic Filter, Threshold=3.0, Cutoff=0.1%, BG=3/1.0,
Peak-Top=Summit

| # | 2-Theta | d(A) | Height | I % | Area | I % | FWHM |
|---|---|---|---|---|---|---|---|
| 1 | 7.134 | 12.3814 | 3460 | 26.8 | 26971 | 8.8 | 0.161 |
| 2 | 8.472 | 10.4288 | 6807 | 52.8 | 64522 | 21.0 | 0.176 |
| 3 | 10.247 | 8.6251 | 5512 | 42.8 | 49102 | 16.0 | 0.171 |
| 4 | 11.528 | 7.6697 | 2505 | 19.4 | 14912 | 4.8 | 0.147 |
| 5 | 12.280 | 7.2020 | 8156 | 63.3 | 69364 | 22.5 | 0.159 |
| 6 | 12.750 | 6.9370 | 1695 | 13.2 | 10097 | 3.3 | 0.198 |
| 7 | 13.976 | 6.3314 | 5645 | 43.8 | 53905 | 17.5 | 0.189 |
| 8 | 14.274 | 6.2000 | 1488 | 11.5 | 11071 | 3.6 | 0.286 |
| 9 | 15.825 | 5.5953 | 3044 | 23.6 | 19608 | 6.4 | 0.157 |
| 10 | 16.693 | 5.3066 | 2533 | 19.7 | 9863 | 3.2 | 0.141 |
| 11 | 17.209 | 5.1486 | 6499 | 50.4 | 56001 | 18.2 | 0.183 |
| 12 | 17.545 | 5.0506 | 2258 | 17.5 | 6593 | 2.1 | 0.160 |
| 13 | 17.877 | 4.9576 | 4956 | 38.5 | 39857 | 13.0 | 0.207 |
| 14 | 18.471 | 4.7995 | 12452 | 96.6 | 134485 | 43.7 | 0.196 |
| 15 | 18.744 | 4.7303 | 9841 | 76.4 | 110996 | 36.1 | 0.210 |
| 16 | 19.282 | 4.5995 | 1613 | 12.5 | 524 | 0.2 | 0.027 |
| 17 | 21.032 | 4.2204 | 2209 | 17.1 | 9030 | 2.9 | 0.162 |
| 18 | 21.583 | 4.1139 | 3550 | 27.5 | 37160 | 12.1 | 0.270 |
| 19 | 22.114 | 4.0163 | 4660 | 36.2 | 38912 | 12.6 | 0.193 |
| 20 | 22.807 | 3.8959 | 1756 | 13.6 | 2275 | 0.7 | 0.117 |
| 21 | 23.181 | 3.8338 | 2898 | 22.5 | 3731 | 1.2 | 0.072 |
| 22 | 23.594 | 3.7677 | 7006 | 54.4 | 74001 | 24.1 | 0.216 |
| 23 | 24.167 | 3.6796 | 12887 | 100.0 | 307625 | 100.0 | 0.448 |
| 24 | 25.664 | 3.4682 | 8874 | 68.9 | 84699 | 27.5 | 0.205 |
| 25 | 26.533 | 3.3566 | 5010 | 38.9 | 58015 | 18.9 | 0.306 |
| 26 | 27.299 | 3.2642 | 3035 | 23.6 | 18810 | 6.1 | 0.221 |
| 27 | 27.634 | 3.2254 | 1954 | 15.2 | 6830 | 2.2 | 0.239 |
| 28 | 28.049 | 3.1785 | 2541 | 19.7 | 13129 | 4.3 | 0.197 |
| 29 | 29.234 | 3.0524 | 3277 | 25.4 | 21615 | 7.0 | 0.239 |
| 30 | 29.825 | 2.9932 | 4235 | 32.9 | 31150 | 10.1 | 0.227 |
| 31 | 30.276 | 2.9496 | 4210 | 32.7 | 41455 | 13.5 | 0.305 |
| 32 | 30.789 | 2.9017 | 3478 | 27.0 | 10213 | 3.3 | 0.129 |
| 33 | 31.181 | 2.8660 | 2056 | 16.0 | 3869 | 1.3 | 0.156 |
| 34 | 31.894 | 2.8036 | 1733 | 13.4 | 4898 | 1.6 | 0.229 |
| 35 | 32.762 | 2.7313 | 3023 | 23.5 | 28609 | 9.3 | 0.288 |
| 36 | 34.005 | 2.6342 | 2301 | 17.9 | 15755 | 5.1 | 0.287 |
| 37 | 34.576 | 2.5920 | 2473 | 19.2 | 41074 | 13.4 | 0.529 |
| 38 | 34.910 | 2.5680 | 2396 | 18.6 | 18865 | 6.1 | 0.269 |
| 39 | 36.191 | 2.4799 | 1764 | 13.7 | 11399 | 3.7 | 0.289 |
| 40 | 37.492 | 2.3968 | 2558 | 19.8 | 33014 | 10.7 | 0.386 |
| 41 | 38.517 | 2.3354 | 2149 | 16.7 | 13248 | 4.3 | 0.246 |
| 42 | 39.447 | 2.2825 | 1759 | 13.6 | 9752 | 3.2 | 0.320 |
| 43 | 40.805 | 2.2095 | 1867 | 14.5 | 18285 | 5.9 | 0.404 |
| 44 | 42.397 | 2.1302 | 1567 | 12.2 | 2902 | 0.9 | 0.217 |
| 45 | 42.875 | 2.1076 | 1846 | 14.3 | 20031 | 6.5 | 0.515 |
| 46 | 43.937 | 2.0590 | 1493 | 11.6 | 6252 | 2.0 | 0.310 |

Peak Search Report (52 Peaks, Max P/N = 49.5)
PEAK: 35-pts/Parabolic Filter, Threshold=3.0, Cutoff=0.1%, BG=3/1.0, Peak-Top=Summit

| # | 2-Theta | d(A) | Height | I % | Area | I % | FWHM |
|---|---|---|---|---|---|---|---|
| 1 | 7.150 | 12.3523 | 2679 | 22.4 | 21443 | 15.3 | 0.160 |
| 2 | 8.491 | 10.4053 | 5476 | 45.8 | 48557 | 34.6 | 0.163 |
| 3 | 10.265 | 8.6101 | 4376 | 36.6 | 38995 | 27.8 | 0.169 |
| 4 | 11.540 | 7.6615 | 1580 | 13.2 | 8277 | 5.9 | 0.135 |
| 5 | 12.281 | 7.2014 | 5423 | 45.3 | 44560 | 31.7 | 0.153 |
| 6 | 12.677 | 6.9770 | 1028 | 8.6 | 5102 | 3.6 | 0.184 |
| 7 | 13.994 | 6.3232 | 3717 | 31.1 | 32019 | 22.8 | 0.171 |
| 8 | 14.344 | 6.1699 | 863 | 7.2 | 2991 | 2.1 | 0.168 |
| 9 | 15.804 | 5.6029 | 2322 | 19.4 | 13082 | 9.3 | 0.132 |
| 10 | 16.653 | 5.3190 | 1727 | 14.4 | 4851 | 3.5 | 0.085 |
| 11 | 17.206 | 5.1493 | 4907 | 41.0 | 33924 | 24.1 | 0.145 |
| 12 | 17.538 | 5.0526 | 1335 | 11.2 | 1573 | 1.1 | 0.083 |
| 13 | 17.859 | 4.9625 | 3394 | 28.4 | 26755 | 19.0 | 0.190 |
| 14 | 18.468 | 4.8002 | 9815 | 82.0 | 97587 | 69.5 | 0.174 |
| 15 | 18.724 | 4.7352 | 7939 | 66.3 | 71710 | 51.0 | 0.163 |
| 16 | 19.352 | 4.5830 | 1078 | 9.0 | 2124 | 1.5 | 0.126 |
| 17 | 21.016 | 4.2236 | 1731 | 14.5 | 7181 | 5.1 | 0.135 |
| 18 | 21.563 | 4.1177 | 2692 | 22.5 | 20356 | 14.5 | 0.181 |
| 19 | 22.135 | 4.0125 | 3439 | 28.7 | 27637 | 19.7 | 0.178 |
| 20 | 22.806 | 3.8961 | 1250 | 10.4 | 1843 | 1.3 | 0.090 |
| 21 | 23.184 | 3.8334 | 2219 | 18.5 | 5519 | 3.9 | 0.092 |
| 22 | 23.593 | 3.7677 | 6251 | 52.2 | 47897 | 34.1 | 0.148 |
| 23 | 24.068 | 3.6945 | 11967 | 100.0 | 140476 | 100.0 | 0.217 |
| 24 | 24.541 | 3.6244 | 6680 | 55.8 | 92994 | 66.2 | 0.298 |
| 25 | 25.585 | 3.4788 | 7377 | 61.6 | 64896 | 46.2 | 0.174 |
| 26 | 26.199 | 3.3987 | 2812 | 23.5 | 22505 | 16.0 | 0.221 |
| 27 | 26.553 | 3.3541 | 3971 | 33.2 | 30018 | 21.4 | 0.173 |
| 28 | 27.263 | 3.2684 | 2356 | 19.7 | 12514 | 8.9 | 0.157 |
| 29 | 27.621 | 3.2268 | 1463 | 12.2 | 7317 | 5.2 | 0.236 |
| 30 | 27.988 | 3.1853 | 2067 | 17.3 | 11633 | 8.3 | 0.176 |
| 31 | 29.233 | 3.0525 | 2773 | 23.2 | 16240 | 11.6 | 0.166 |
| 32 | 29.430 | 3.0325 | 2310 | 19.3 | 21263 | 15.1 | 0.277 |
| 33 | 29.766 | 2.9990 | 3751 | 31.3 | 26910 | 19.2 | 0.170 |
| 34 | 30.219 | 2.9551 | 3262 | 27.3 | 18728 | 13.3 | 0.161 |
| 35 | 30.789 | 2.9017 | 2819 | 23.6 | 18164 | 12.9 | 0.182 |
| 36 | 31.084 | 2.8747 | 1648 | 13.8 | 6588 | 4.7 | 0.175 |
| 37 | 31.894 | 2.8036 | 1416 | 11.8 | 3663 | 2.6 | 0.133 |
| 38 | 32.762 | 2.7312 | 2904 | 24.3 | 25892 | 18.4 | 0.217 |
| 39 | 33.705 | 2.6570 | 1382 | 11.5 | 7232 | 5.1 | 0.238 |
| 40 | 34.024 | 2.6328 | 1891 | 15.8 | 12287 | 8.7 | 0.216 |
| 41 | 34.574 | 2.5921 | 2112 | 17.6 | 17116 | 12.2 | 0.240 |
| 42 | 34.929 | 2.5666 | 1676 | 14.0 | 15198 | 10.8 | 0.297 |
| 43 | 36.190 | 2.4800 | 1558 | 13.0 | 10105 | 7.2 | 0.214 |
| 44 | 37.234 | 2.4128 | 1485 | 12.4 | 11592 | 8.3 | 0.266 |
| 45 | 37.492 | 2.3969 | 2277 | 19.0 | 17493 | 12.5 | 0.200 |
| 46 | 38.478 | 2.3377 | 1598 | 13.4 | 14068 | 10.0 | 0.306 |
| 47 | 39.465 | 2.2814 | 1323 | 11.1 | 9076 | 6.5 | 0.290 |
| 48 | 40.882 | 2.2056 | 1421 | 11.9 | 15389 | 11.0 | 0.389 |
| 49 | 42.362 | 2.1319 | 1220 | 10.2 | 10357 | 7.4 | 0.445 |
| 50 | 42.893 | 2.1067 | 1415 | 11.8 | 18269 | 13.0 | 0.484 |
| 51 | 43.310 | 2.0874 | 1104 | 9.2 | 1613 | 1.1 | 0.114 |
| 52 | 43.976 | 2.0573 | 1185 | 9.9 | 6729 | 4.8 | 0.263 |

Peak Search Report (52 Peaks, Max P/N = 67.0)
PEAK: 35-pts/Parabolic Filter, Threshold=3.0, Cutoff=0.1%, BG=3/1.0, Peak-Top=Summit

| # | 2-Theta | d(A) | Height | I % | Area | I % | FWHM |
|---|---|---|---|---|---|---|---|
| 1 | 7.073 | 12.4880 | 4777 | 24.5 | 36405 | 19.3 | 0.151 |
| 2 | 8.317 | 10.6220 | 19480 | 100.0 | 172669 | 91.6 | 0.155 |
| 3 | 10.092 | 8.7579 | 7118 | 36.5 | 63102 | 33.5 | 0.167 |
| 4 | 11.468 | 7.7098 | 2392 | 12.3 | 11854 | 6.3 | 0.128 |
| 5 | 12.199 | 7.2491 | 5578 | 28.6 | 43999 | 23.3 | 0.156 |
| 6 | 12.848 | 6.8846 | 2104 | 10.8 | 10934 | 5.8 | 0.149 |
| 7 | 13.756 | 6.4322 | 8230 | 42.2 | 76963 | 40.8 | 0.175 |
| 8 | 14.171 | 6.2447 | 2380 | 12.2 | 29767 | 15.8 | 0.323 |
| 9 | 15.810 | 5.6009 | 3879 | 19.9 | 27056 | 14.4 | 0.151 |
| 10 | 16.715 | 5.2996 | 3923 | 20.1 | 27797 | 14.8 | 0.145 |
| 11 | 16.990 | 5.2144 | 4758 | 24.4 | 41990 | 22.3 | 0.184 |
| 12 | 17.229 | 5.1424 | 5170 | 26.5 | 45771 | 24.3 | 0.184 |
| 13 | 17.681 | 5.0120 | 6487 | 33.3 | 60844 | 32.3 | 0.217 |
| 14 | 18.373 | 4.8249 | 11581 | 59.5 | 105706 | 56.1 | 0.174 |
| 15 | 18.705 | 4.7399 | 9409 | 48.3 | 95560 | 50.7 | 0.186 |
| 16 | 19.172 | 4.6256 | 2247 | 11.5 | -1600 | -0.8 | 0.020 |
| 17 | 20.282 | 4.3748 | 1280 | 6.6 | 2012 | 1.1 | 0.126 |
| 18 | 20.933 | 4.2402 | 2307 | 11.8 | 6620 | 3.5 | 0.101 |
| 19 | 21.683 | 4.0953 | 9635 | 49.5 | 109317 | 58.0 | 0.214 |
| 20 | 22.732 | 3.9085 | 2112 | 10.8 | 3791 | 2.0 | 0.076 |
| 21 | 23.052 | 3.8550 | 1989 | 10.2 | 2361 | 1.3 | 0.077 |
| 22 | 23.436 | 3.7928 | 5901 | 30.3 | 44880 | 23.8 | 0.147 |
| 23 | 23.713 | 3.7491 | 5951 | 30.5 | 70127 | 37.2 | 0.269 |
| 24 | 24.422 | 3.6417 | 17203 | 88.3 | 188447 | 100.0 | 0.217 |
| 25 | 24.934 | 3.5681 | 3863 | 19.8 | 18381 | 9.8 | 0.172 |
| 26 | 25.135 | 3.5401 | 4168 | 21.4 | 20120 | 10.7 | 0.157 |
| 27 | 25.843 | 3.4447 | 11076 | 56.9 | 97470 | 51.7 | 0.175 |
| 28 | 26.296 | 3.3863 | 6320 | 32.4 | 105859 | 56.2 | 0.388 |
| 29 | 27.064 | 3.2919 | 4303 | 22.1 | 47899 | 25.4 | 0.297 |
| 30 | 28.130 | 3.1696 | 2745 | 14.1 | 17030 | 9.0 | 0.186 |
| 31 | 29.056 | 3.0706 | 3023 | 15.5 | 23009 | 12.2 | 0.222 |
| 32 | 29.903 | 2.9856 | 4857 | 24.9 | 61254 | 32.5 | 0.292 |
| 33 | 30.337 | 2.9438 | 8333 | 42.8 | 117902 | 62.6 | 0.281 |
| 34 | 31.243 | 2.8605 | 2117 | 10.9 | 9692 | 5.1 | 0.183 |
| 35 | 31.734 | 2.8174 | 2152 | 11.0 | 15638 | 8.3 | 0.267 |
| 36 | 32.659 | 2.7396 | 2162 | 11.1 | 22423 | 11.9 | 0.355 |
| 37 | 32.880 | 2.7217 | 2251 | 11.6 | 21233 | 11.3 | 0.291 |
| 38 | 33.823 | 2.6480 | 2071 | 10.6 | 18771 | 10.0 | 0.353 |
| 39 | 34.317 | 2.6110 | 2515 | 12.9 | 49779 | 26.4 | 0.578 |
| 40 | 34.536 | 2.5949 | 2176 | 11.2 | 29181 | 15.5 | 0.423 |
| 41 | 35.876 | 2.5010 | 1546 | 7.9 | 6390 | 3.4 | 0.203 |
| 42 | 36.523 | 2.4582 | 1333 | 6.8 | 1766 | 0.9 | 0.143 |
| 43 | 37.275 | 2.4103 | 2810 | 14.4 | 36853 | 19.6 | 0.360 |
| 44 | 37.867 | 2.3739 | 1674 | 8.6 | 5461 | 2.9 | 0.217 |
| 45 | 38.556 | 2.3331 | 1527 | 7.8 | 7329 | 3.9 | 0.342 |
| 46 | 39.265 | 2.2926 | 1976 | 10.1 | 11732 | 6.2 | 0.274 |
| 47 | 40.153 | 2.2439 | 2824 | 14.5 | 28808 | 15.3 | 0.293 |
| 48 | 41.278 | 2.1853 | 1491 | 7.7 | 4098 | 2.2 | 0.165 |
| 49 | 41.965 | 2.1511 | 1425 | 7.3 | 5504 | 2.9 | 0.286 |
| 50 | 42.559 | 2.1225 | 2239 | 11.5 | 17089 | 9.1 | 0.268 |
| 51 | 43.010 | 2.1012 | 1909 | 9.8 | 23217 | 12.3 | 0.545 |
| 52 | 43.912 | 2.0601 | 1426 | 7.3 | 3019 | 1.6 | 0.233 |

FIG 6b

CRYSTALS OF PRASUGREL HYDROBROMATE

CROSS REFERENCE TO RELATED APPLICATIONS

This application is the national stage entry under 35 USC 371 for PCT/CN2010/071464, filed Mar. 31, 2010, which claims the benefit of the Mar. 31, 2009 priority date of Chinese Application No. 200910030050.3. The contents of both the foregoing applications are incorporated herein by reference.

FIELD OF THE INVENTION

The present invention relates to crystals of pharmaceutical compounds. In particular, the present invention relates to crystals of prasugrel hydrobromate, particularly acetic acid solvated crystals of prasugrel hydrobromate. The present invention further relates to a method of preparing the crystals of prasugrel hydrobromate, crystal compositions and pharmaceutical compositions comprising the crystals of prasugrel hydrobromate, and use thereof.

BACKGROUND OF THE INVENTION

Vascular diseases such as thrombus and embolism are pathophysiologically initiated by platelet activation firstly. Therefore, antiplatelet therapy is crucial for the prevention of vascular diseases. ADP (adenosine diphosphate) is an important pathologic and physiologic platelet agonist. When a blood vessel is damaged, ADP is released from damaged cells and activated platelets to the blood, and then acts on other platelets. ADP receptor antagonists inhibit the attachment between the fibrinogen and the platelet membrane GPIIb/IIIa, activate platelet adenylate cyclase, and increase cAMP (cyclic adenosine monophosphate) level in platelets and thereby inhibit platelets mainly by inhibiting platelet membrane ADP receptor expression, binding and activity.

Prasugrel (formula I), a new generation of ADP receptor antagonist, is a novel prodrug-type antiplatelet drug (CN1074446A). For ADP-induced platelet aggregation in rats, oral administration of prasugrel is ten times more potent than that of ADP receptor antagonist, clopidogrel, which is available from the market.

I

The plasma concentration of active metabolites of prasugrel is ten times higher than that of clopidogrel as well, indicating that the greater efficacy of prasugrel may result from its faster metabolic rate.

CN1452624A discloses prasugrel hydrochloride and maleate, which exhibit good activity in oral absorption, metabolization, and inhibition of platelet aggregation and weak toxicity.

CN101255169A discloses prasugrel hydrobromate, which exhibits improved water solubility and thermal stability as compared to hydrochloride, and unsatisfactory performance in high humidity and light stability. However, for pharmaceutical compounds, stability is one of important features thereof, and good stability often has a beneficial effect on industrial processes including preparation, storage, usage (manufacturing raw material into formulation) and the like.

SUMMARY OF THE INVENTION

In one aspect of the invention, there is provided a crystal A of prasugrel hydrobromate having formula II,

II wherein: Sol is a solvent;
m is 0.1~2, preferably 0.5~1.5, more preferably 1.
In another aspect of the invention, there is provided a crystal A of prasugrel hydrobromate having formula II,

II wherein: Sol is acetic acid;
m is 1.
In another aspect of the invention, there is provided a crystal B of prasugrel hydrobromate having formula III.

III

In another aspect of the invention, there is provided a crystal A composition, comprising the crystal A as defined above in an amount of 60% or more, preferably 90% or more, more preferably 95% or more, and most preferably 99% or more, by weight.

In another aspect of the invention, there is provided a crystal B composition, comprising the crystal B as defined above in an amount of 60% or more, preferably 90% or more, more preferably 95% or more, and most preferably 99% or more, by weight.

In another aspect of the invention, there is provided a pharmaceutical composition comprising a therapeutically effect amount of the crystal A or B as defined above, or the crystal A or B composition as defined above.

In another aspect of the invention, there is provided a method for preventing or treating diseases associated with thrombus or embolism in an animal, comprising administering to the animal in need thereof a therapeutically effective amount of the crystal A or B as defined above, the crystal A or B composition as defined above or the pharmaceutical composition comprising prasugrel hydrobromate as defined above.

In another aspect of the invention, there is provided use of the crystal A or B as defined above, the crystal A or B composition as defined above and the pharmaceutical composition comprising prasugrel hydrobromate as defined above in the preparation of a medicament for the prophylaxis or treatment of diseases associated with thrombus or embolism.

DETAILED DESCRIPTION OF THE INVENTION

In one aspect of the invention, there is provided a crystal A of prasugrel hydrobromate having formula II,

II wherein: Sol is a solvent;
m is 0.1~2, preferably 0.5~1.5, more preferably 1.

Solvents that can be used in the present invention include, but are not limited to, ethers such as diethyl ether, diisopropyl ether, tetrahydrofuran and dimethoxyethane; esters such as methyl acetate, ethyl acetate and ethyl formate; ketones such as acetone and butanone; nitriles such as acetonitrile and propionitrile; dipolar aprotic solvents such as DMF and DMSO; acidic solvents such as formic acid and acetic acid; and water.

In one embodiment, the solvent of the invention is selected from the group consisting of diethyl ether and diisopropyl ether. In another embodiment, the solvent of the invention is ethyl acetate. In another embodiment, the solvent of the invention is acetone. In another embodiment, the solvent of the invention is acetonitrile. In another embodiment, the solvent of the invention is DMSO. In another embodiment, the solvent of the invention is acetic acid. In another embodiment, the solvent of the invention is water.

In another aspect of the invention, there is provided a crystal A of prasugrel hydrobromate having formula II,

II wherein: Sol is acetic acid;
m is 1.

In some embodiments of the aspect, the crystal A of prasugrel hydrobromate of the invention is of orthorhombic structure, and the space group thereof is Pnma; the lattice parameters thereof approximately are: a=15.33 Å, b=7.39 Å, c=20.82 Å, α=β=γ=90°; and the lattice volume thereof=2356.89 Å³.

In the XRPD (X-ray powder diffraction) pattern of the crystal A of prasugrel hydrobromate of the invention measured with Cu-Kα radiation, diffraction peaks expressed as interplanar spacing d are found at about 10.43 Å, 8.63 Å, 7.20 Å, 6.33 Å, 5.15 Å, and 3.47 Å, typically about 10.43 Å, 8.63 Å, 7.20 Å, 6.33 Å, 5.15 Å, 4.80 Å, 4.73 Å, 3.77 Å, 3.68 Å, and 3.47 Å, more typically about 12.38 Å, 10.43 Å, 8.63 Å, 7.20 Å, 6.33 Å, 5.15 Å, 4.96 Å, 4.80 Å, 4.73 Å, 4.02 Å, 3.77 Å, 3.68 Å, 3.47 Å, 3.36 Å, 2.99 Å, and 2.95 Å, and still more typically about 12.38 Å, 10.43 Å, 8.63 Å, 7.67 Å, 7.20 Å, 6.94 Å, 6.33 Å, 5.60 Å, 5.31 Å, 5.15 Å, 4.96 Å, 4.80 Å, 4.73 Å, 4.22 Å, 4.11 Å, 4.02 Å, 3.83 Å, 3.77 Å, 3.68 Å, 3.47 Å, 3.36 Å, 3.26 Å, 3.23 Å, 2.99 Å, 2.95 Å, 2.90 Å, 2.73 Å, and 2.40 Å.

In the IR (infrared absorption spectrum) of the crystal A of prasugrel hydrobromate of the invention, absorption peaks are found at about 1719 and 1763 cm$^{-1}$.

In the DSC (differential scanning calorimetry) of the crystal A of prasugrel hydrobromate of the invention, the starting temperature of the endothermic peak is about 128° C.

In another aspect of the invention, there is provided a crystal B of prasugrel hydrobromate having formula III.

III

The crystal B of prasugrel hydrobromate of the invention is of orthorhombic structure, and the space group thereof is Pnma; the lattice parameters thereof approximately are: a=15.42 Å, b=7.29 Å, c=21.24 Å, α=β=γ=90°; and the lattice volume thereof=2387.09 Å$^3$.

In the XRPD (X-ray powder diffraction) pattern of the crystal B of prasugrel hydrobromate of the invention measured with Cu-Kα radiation, diffraction peaks expressed as interplanar spacing d are found at about 10.62 Å, 6.43 Å, 4.82 Å, 3.64 Å, and 3.44 Å, typically about 10.62 Å, 8.76 Å, 6.43 Å, 4.82 Å, 4.74 Å, 4.10 Å, 3.64 Å, 3.44 Å, and 2.94 Å, more typically about 12.49 Å, 10.62 Å, 8.76 Å, 7.71 Å, 7.25 Å, 6.43 Å, 5.01 Å, 4.82 Å, 4.74 Å, 4.10 Å, 3.64 Å, 3.44 Å, 3.39 Å, and 2.94 Å, and still more typically about 12.49 Å, 10.62 Å, 8.76 Å, 7.71 Å, 7.25 Å, 6.88 Å, 6.43 Å, 5.60 Å, 5.30 Å, 5.21 Å, 5.14 Å, 5.01 Å, 4.82 Å, 4.74 Å, 4.10 Å, 3.79 Å, 3.75 Å, 3.64 Å, 3.57 Å, 3.54 Å, 3.44 Å, 3.39 Å, 3.17 Å, 3.07 Å, 2.99 Å, 2.94 Å, 2.61 Å, 2.41 Å, and 2.24 Å.

In the IR (infrared absorption spectrum) of the crystal B of prasugrel hydrobromate of the invention, absorption peaks are found at about 1713 and 1762 cm$^{-1}$.

It is to be understood that, in XRPD, a diffraction pattern obtained from a crystal compound is generally characteristic of a particular crystal form. However, relative intensities of bands (especially at low angles) may vary with the effect of dominant orientation resulting from difference in crystallization conditions, particle sizes and other test conditions. As a result, relative intensities of diffraction peaks are not characteristic of the particular crystal form, and one should focus on positions of peaks rather than relative intensities while determining whether a crystal form is the same as a known one. In XPRD, the peak position is generally expressed as diffraction angle 2θ or interplanar spacing d. Since 2θ is relevant to wavelength of the incident X ray, interplanar spacing d is more representative. They have a simple conversion relationship therebetween: d=λ/2 sin θ, in which d represents the interplanar spacing, λ represents wavelength of the incident X ray (for Cu-Kα, λ=1.54187 Å), and θ represents diffraction angle. For the same crystal form of the same compound, their XPRDs are similar as a whole, and the error of d values indicating peak positions is general within ±2%, mostly no more than ±1%. On the other hand, the error of relative intensities may be larger, but variation trend are identical. In addition, since it is not a single diffracted ray but a particular set of "d-I/I$_1$" data that represents one phase, one should keep holistic thinking when determining whether the crystal forms are identical. Moreover, in the identification of a mixture, since factors such as decreased content can result in absence of some diffracted rays, there is no need to refer to the total bands as observed in highly pure samples. In this case, even one band may be characteristic of the given crystal.

DSC measures the transition temperature of a crystal while it absorbs or releases heat due to crystal structure alteration or crystal melting. For the same crystal form of the same compound, in continuous analysis, the errors of thermal transition temperature and melting point are typically within ±5° C., generally within ±3° C. DSC provides a supplemental method for identifying different crystal forms. Different crystal forms can be identified by different transition temperatures thereof. It is to be noted that for a mixture, the DSC peak or melting point thereof might vary within a broader scope. In addition, melting temperature is closely related with increasing rate of temperature, as decomposition occurs during melting of a substance.

IR measures infrared absorption resulting from particular chemical bonds in a molecule which are associated with groups vibrating under light. Since electrical environments of intramolecular covalent bonds in different crystal forms are different, strength of covalent bonds may be different as well, which inevitably causes different IR spectra for different crystal forms.

In another aspect of the invention, there is provided a crystal A composition, comprising the crystal A as defined above in an amount of 60% or more, preferably 90% or more, more preferably 95% or more, and most preferably 99% or more, by weight. In addition to crystal A, the crystal A composition may further comprise a small amount of other crystal forms and amorphous prasugrel hydrobromate.

In another aspect of the invention, there is provided a crystal B composition, comprising the crystal B as defined above in an amount of 60% or more, preferably 90% or more, more preferably 95% or more, and most preferably 99% or more, by weight. In addition to crystal B, the crystal B composition may further comprise a small amount of other crystal forms and amorphous prasugrel hydrobromate.

The crystal A or crystal A composition of prasugrel hydrobromate of the present invention can be prepared by the following methods:

Method 1: prasugrel (the compound of formula I) as a starting material (please refer to CN1074446A) is dissolved in a suitable organic solvent under stirring. A substance containing hydrogen bromide and a substance containing acetic acid are simultaneously or successively added slowly at 0~40° C., and the reaction is carried out for 5 min~2 h. After completion of the reaction, the mixture is stirred at 0~40° C. for another 1~10 h. The mixture is cooled down to crystallize, filtered and the resultant crystal is washed with a small amount of acetone. The crystal is dried at 30~60° C. under reduced pressure for 1~10 h. The suitable organic solvent may be acetone, acetic acid, or mixture thereof, preferably the mixture of acetone and acetic acid. The amount of the organic solvent is 5~20 ml/g prasugrel, preferably 8~12 ml/g prasugrel, the molar ratio of prasugrel to hydrogen bromide is 1:(0.5~5), and the reaction time is preferably 5~15 min. After completion of the reaction, preferably, the mixture is stirred for 1~3 h, the temperature for crystallization is 0~25° C., and the temperature and time for drying under reduced pressure is 60° C. and 4 h, respectively.

Method 2: prasugrel hydrobromate as a starting material (please refer to CN101255169A) is dissolved in a suitable organic solvent, and then acetic acid (or a substance containing acetic acid) is added. Alternatively, prasugrel hydrobromate is dissolved in acetic acid directly. Heating can be performed to facilitate the dissolution. The mixture is stirred at 0~30° C. for 1~10 h, and the obtained crystal is filtered and washed with a small amount of acetone. The crystal is dried at 30~60° C. under reduced pressure for 1~10 h. The suitable organic solvent is preferably acetone, acetic acid, or mixture thereof. The amount of the organic solvent is 5~20 ml/g prasugrel, preferably 8~12 ml/g prasugrel. Preferably, the mixture is stirred for 1~3 h, the temperature for crystallization is 0~25° C., and the temperature and time for drying under reduced pressure is 60° C. and 4 h, respectively.

Method 3: the acetic acid solvated crystal of prasugrel hydrobromate obtained by Method 1 or 2 as mentioned above is added to a suitable amount of acetic acid, and dissolved with heating. The mixture is cooled down to room temperature under stirring, and stirred for another 1-10 h. The precipitated crystal is filtered and washed with a small amount of acetone. The crystal is dried under reduced pressure at 30~60° C. for 1~10 h. The amount of acetic acid is 5~20 ml/g prasugrel, preferably 8~12 ml. Preferably, heating temperature is 40~90° C., stirring time is 1~3 h, and the temperature and time for drying under reduced pressure is 60° C. and 4 h, respectively.

The crystal B or crystal B composition of prasugrel hydrobromate of the present invention can be prepared by the following method:

Method 4: prasugrel (the compound of formula I) as a starting material (please refer to CN1074446A) is dissolved in acetone. The aqueous solution containing hydrogen bromide is added slowly at 0~40° C. and the reaction is carried out for 5 min~2 h to crystallize. After completion of the reaction, the mixture is stirred at 0~40° C. for another 1~10 h. The mixture is filtered and the crystal is washed with a small amount of acetone. The crystal is then dried at 30~60° C. under reduced pressure for 1~10 h. The amount of acetone is 5~20 ml/g prasugrel, preferably 10~15 ml, the molar ratio of prasugrel to hydrogen bromide is 1:(0.5~5), and the reaction time is preferably 5~15 min. After completion of the reaction, preferably, the mixture is stirred for 1~3 h, the temperature is 0~room temperature, and the temperature and time for drying under reduced pressure is 60° C. and 4 h, respectively.

In another aspect of the invention, there is provided a pharmaceutical composition comprising a therapeutically effect amount of a crystal of prasugrel hydrobromate having formular II, especially the crystal A or B as defined above, or the crystal A or B composition as defined above.

In addition to the crystal A or B as defined above, or the crystal A or B composition as defined above as active ingredients, the pharmaceutical composition of prasugrel hydrobromate of the present invention may further comprise suitable pharmacological acceptable excipients, diluents and the like for the administration to an animal subject, such as a human patient, through various administration routes including oral and parenteral administration, such as intravenous, intramuscular, topical, or subcutaneous administration. The crystals, crystal compositions and pharmaceutical compositions of the present invention are preferably for oral administration.

Therefore, prasugrel hydrobromate of the present invention can be administered systematically such as orally in combination with pharmaceutically acceptable vehicles, such as inert diluents or absorbable and edible carriers. They can be encapsulated into hard or soft gelatin capsules, pressed into tablets, or directly mixed into diets for patients. For oral administration, active compounds can be combined with one or more excipients, and formulated as absorbable tablets, buccal tablets, lozenges, capsules, elixir, suspensions, syrups and films, etc.

Such formulations may be prepared according to any well known technique, and may also include the following additives: excipients (such as organic excipients, including glucose derivatives such as lactose, sucrose, glucose, mannitol and sorbitol; starch derivatives such as corn starch, potato starch, α-starch and dextrin; cellulose derivatives such as crystalline cellulose; gum Arabic; dextran; and Pullulan; and inorganic excipients, including silicate derivatives such as light anhydrous silicic acid, synthetic aluminium silicate, calcium silicate and magnesium aluminum silicate; phosphates such as calcium hydrogen phosphate; carbonates such as calcium carbonate; sulfates such as calcium sulfate), lubricants (such as stearic acid and metallic stearates such as calcium stearate and magnesium stearate; talc and waxes such as beeswax and spermaceti; boric acid; adipic acid; sulfates such as sodium sulfate; glycol; fumaric acid; sodium benzoate; DL-leucine; lauryl sulfates such as sodium lauryl sulfate and magnesium lauryl sulfate; silicates such as silicic anhydride and silicic acid hydrate; and the above-described starch derivatives), binders (such as hydroxypropyl cellulose, hydroxypropyl methylcellulose, polyvinylpyrrolidone, polyethylene glycol and the above-described excipients), disintegrants (such as cellulose derivatives including low-substituted hydroxypropyl cellulose, carboxymethyl cellulose, calcium carboxymethyl cellulose and internal-crosslinked sodium carboxymethyl cellulose; chemically modified starch-cellulose compounds such as carboxymethyl starch, sodium carboxymethyl starch and cross-linked polyvinylpyrrolidone; the above-described starch derivatives), emulsifiers (such as colloidal clays including bentonite and Veegum; metal hydroxides such as magnesium hydroxide and aluminium hydroxide; anionic surfactants such as sodium lauryl sulfate and calcium stearate; cationic surfactants such as benzalkonium chloride; and nonionic surfactants such as polyoxyethylene alkyl ether, polyoxyethylene sorbitan fatty acid ester and sucrose fatty acid ester), stabilizers (such as p-hydroxybenzoic esters such as methylparaben and propylparaben; alcohols such as chlorobutanol, benzyl alcohol and phenethyl alcohol; phenols such as benzalkonium chloride, phenol and cresol; thimerosal; dehydroacetic acid; and sorbic acid), correctives (such as sweeteners, souring agents and flavors which are commonly used in the art), and diluents.

In another aspect of the invention, there is provided a method for preventing or treating diseases associated with thrombus or embolism in an animal, comprising administering to the animal in need thereof a therapeutically effective amount of the crystal A or B as defined above, the crystal A or B composition as defined above or the pharmaceutical composition comprising prasugrel hydrobromate as defined above.

In some embodiments, the disease is thrombosis. In some embodiments, the disease is embolism. The crystals, crystal compositions and pharmaceutical compositions of the present invention are preferably administered to an endotherm, more preferably a human.

Although the dose of the crystal A or B, crystal A or B composition as active ingredients in the pharmaceutical composition comprising prasugrel hydrobromate may vary according to the symptom, age and the like, it may be administered to an adult 1 to 7 times within a period of 1 to 7 days depending on severity of the patient's symptoms. For oral administration, the amount of active ingredients in one unit dosage may be from 0.1 mg to 1000 mg, preferably from 1 mg to 500 mg.

In another aspect of the invention, there is provided use of the crystal A or B as defined above, the crystal A or B composition as defined above and the pharmaceutical composition comprising prasugrel hydrobromate as defined above in the preparation of a medicament for the prophylaxis or treatment of diseases associated with thrombus or embolism.

The following examples are intended to further illustrate the present invention and are not intended to limit the scope of this invention.

EXAMPLES

Example 1

Preparation of Acetic Acid Solvated Crystal of 2-acetoxy-5-(α-cyclopropyl carbonyl-2-fluorobenzyl)-4,5,6,7-tetrahydrothieno[3,2-c]pyridine hydrobromate (crystal A)

2-acetoxy-5-(α-cyclopropylcarbonyl-2-fluorobenzyl)-4,5,6,7-tetrahydrothieno[3,2-c]pyridine (2 g) was dissolved in acetic acid (20 ml), and to the mixture was added dropwise a solution (1.1 g) of hydrogen bromide in acetic acid (40%) with stirring at room temperature of 25° C. A small amount of seed crystals was added to the solution and then the mixture was stirred for 2 hours at the same temperature. The resulting crystals were separated by filtration and washed with a small amount of acetone and then dried at 60° C. under reduced pressure for 4 hours to give the title compound as white crystals (2.29 g, yield 83%).

Example 2

Preparation of Acetic Acid Solvated Crystal of 2-acetoxy-5-(α-cyclopropyl carbonyl-2fluorobenzyl)-4,5,6,7-tetrahydrothieno[3,2-c]pyridine hydrobromate (crystal A)

Acetic acid solvate of prasugrel hydrobromate (0.4 g) was dissolved in acetic acid (4 ml), and the mixture was heated to 70° C. The mixture was stirred for 10 min, and then cooled down to room temperature naturally. The mixture was stirred for another 2 hours. The resulting crystals were separated by filtration and washed with a small amount of acetone and then dried at 60° C. under reduced pressure for 4 hours to give the title compound as white crystals (0.34 g, yield 85%).

Example 3

Preparation of Acetic Acid Solvated Crystal of 2-acetoxy-5-(α-cyclopropyl carbonyl-2-fluorobenzyl)-4,5,6,7-tetrahydrothieno[3,2-c]pyridine hydrobromate (crystal A)

2-acetoxy-5-(α-cyclopropylcarbonyl-2-fluorobenzyl)-4,5,6,7-tetrahydrothieno[3,2-c]pyridine (2 g) was dissolved in a mixture of acetone and acetic acid (30 ml), and a solution (1.1 g) of hydrogen bromide in acetic acid (40%) was added dropwise with stirring at 0° C. A small amount of seed crystals was added and then the mixture was stirred for 2 hours at the same temperature. The resulting crystals were separated by filtration and washed with a small amount of acetone and then dried at 60° C. under reduced pressure for 4 hours to give 2.31 g of the title compound as white crystals.

Example 4

Preparation of Acetic Acid Solvated Crystal of 2-acetoxy-5-(α-cyclopropyl carbonyl-2-fluorobenzyl)-4,5,6,7-tetrahydrothieno[3,2-c]pyridine hydrobromate (crystal A)

2-acetoxy-5-(α-cyclopropylcarbonyl-2-fluorobenzyl)-4,5,6,7-tetrahydrothieno[3,2-c]pyridine hydrobromate (2 g) was added in acetic acid (20 ml), and the mixture was heated to 70° C. The mixture was stirred for 10 min, and then cooled down to room temperature naturally. The mixture was stirred for another 2 hours. The resulting crystals were separated by filtration and washed with a small amount of acetone and then dried at 60° C. under reduced pressure for 4 hours to give 1.8 g of the title compound as white crystals.

Example 5

Preparation of Acetic Acid Solvated Crystal of 2-acetoxy-5-(α-cyclopropyl carbonyl-2-fluorobenzyl)-4,5,6,7-tetrahydrothieno[3,2-c]pyridine hydrobromate (crystal A)

2-acetoxy-5-(α-cyclopropylcarbonyl-2-fluorobenzyl)-4,5,6,7-tetrahydrothieno[3,2-c]pyridine (4 g) was dissolved in acetic acid (60 ml), and hydrogen bromide (40%) aqueous solution (2.16 g) was added dropwise with stirring at room temperature of 25° C. The mixture was stirred for 2 hours at the same temperature. The resulting crystals were separated by filtration and washed with a small amount of acetone and then dried at 60° C. under reduced pressure for 4 hours to give the title compound as white crystals (4.77 g, yield 86.4%).

Example 6

Preparation of Crystal of 2-acetoxy-5-(α-cyclopropylcarbonyl-2-fluorobenzyl)-4,5,6,7-tetrahydrothieno[3,2-c]pyridine hydrobromate (crystal B)

2-acetoxy-5-(α-cyclopropylcarbonyl-2-fluorobenzyl)-4,5,6,7-tetrahydrothieno[3,2-c]pyridine (4 g) was dissolved in 60 ml of acetone. To the solution was added dropwise 1 equivalent of 40% of hydrogen bromide aqueous solution at room temperature, and the mixture was stirred for 5 min, and then the crystals were precipitated. The mixture was stirred for another 2 hours at room temperature. The resulting crystals were separated by vacuum filtration and the filter cake was washed twice with acetone and then dried under reduced pressure to give 4.77 g of the title compound as white crystals.

Example 7

Test of Acetic Acid Solvated Crystal

Figure 1A:
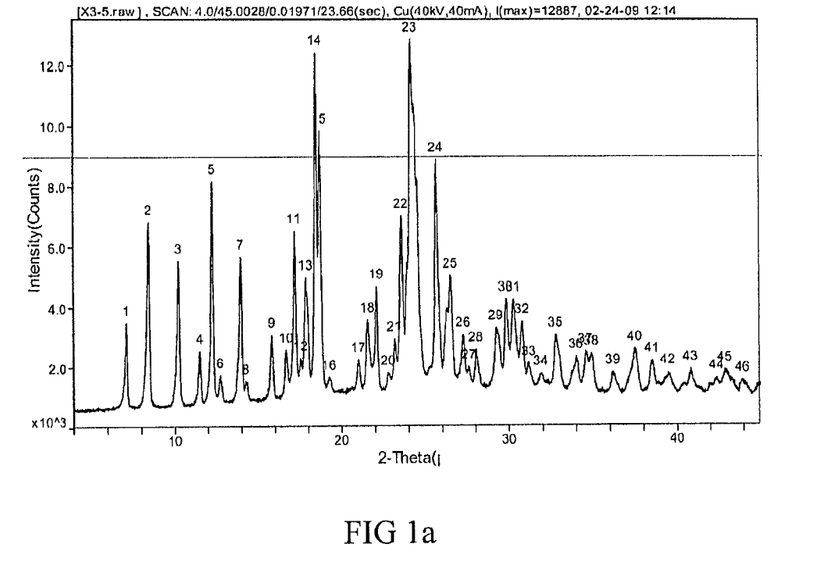
FIG. 1 shows the X-ray powder diffraction pattern of the acetic acid solvated crystal (crystal A) according to example 2.
Figure 2:
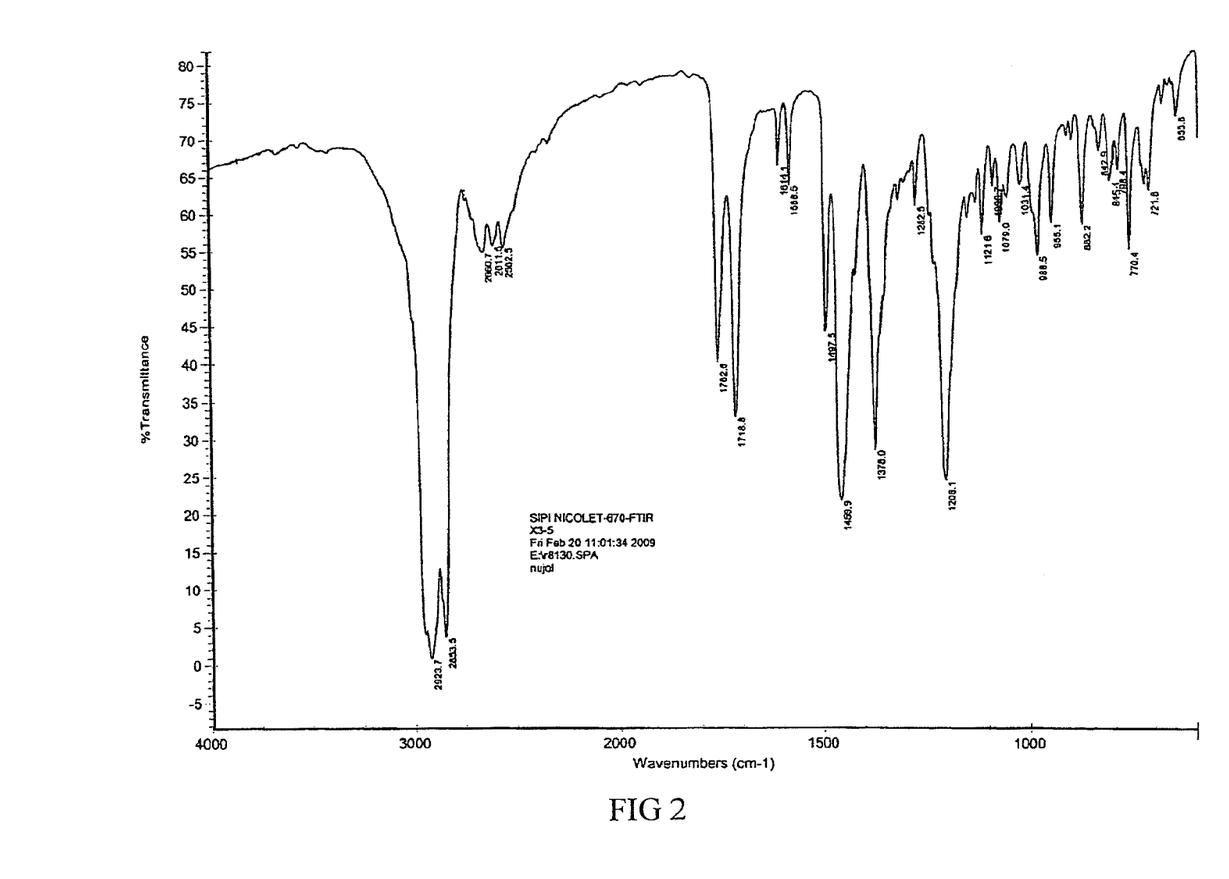
FIG. 2 shows the infrared absorption spectrum of the acetic acid solvated crystal (crystal A) according to example 2.
Figure 3:
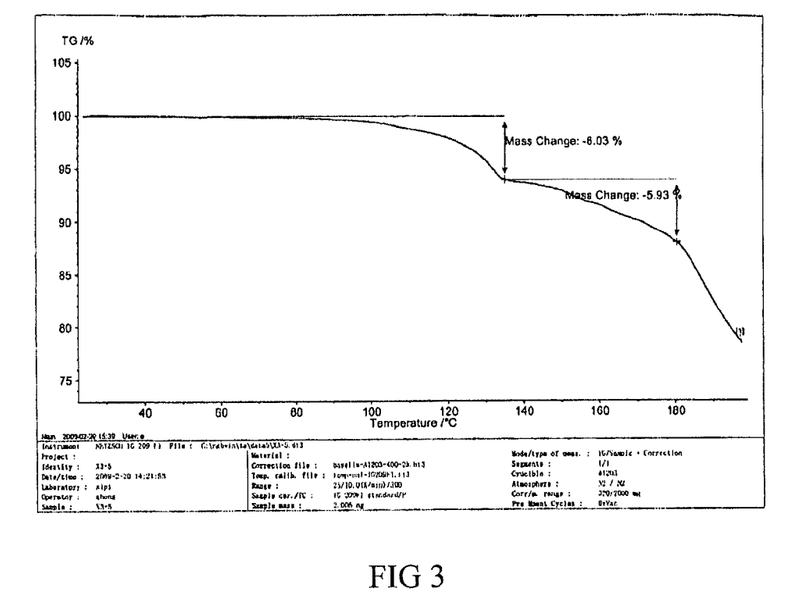
FIG. 3 shows the thermogravimetric analysis (TGA) of the acetic acid solvated crystal (crystal A) according to example 2.
Figure 4:
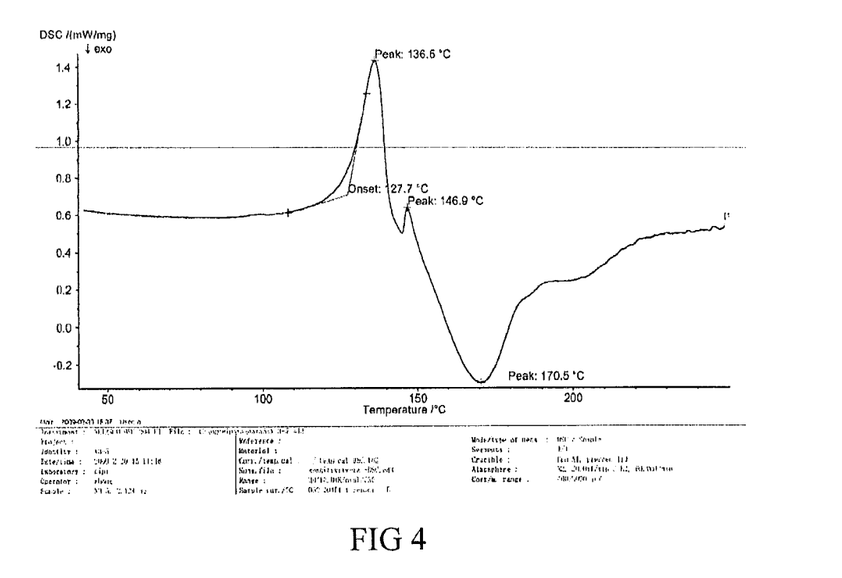
FIG. 4 is the DSC of the acetic acid solvated crystal (crystal A) according to example 2.

Sample: Acetic Acid Solvated Crystal from Example 2 (Crystal A)
X-ray powder diffraction test: Instrument model: Bruker D8 ADVANCE; Light source: Cu-Kα 40 kV 40 mA; graphite monochromator; divergency slit (DS): 1°; anti-scatter slit (SS): 1°; LynxEye array detector, scanning mode: θ/θ, continuous scanning; scanning scope: 3° ~45°, scanning speed: 8°/min. The results are shown in FIG. 1.
Infrared absorption spectroscopy test: 670FI-IR spectrometer of NICOLET Corporation in USA was used, nujol mull method, scanning scope: 400~4000 $cm^{-1}$. The results are shown in FIG. 2.
thermogravimetric analysis (TGA) test: NETZSCH TG 209F1 was used, testing conditions were as follows: an aluminum oxide crucible was used, the scanning scope was from 25° C. to 300° C. under a nitrogen purge at an increasing rate of temperature of 10° C./min and the results are shown in FIG. 3. The weight lost until 180° C. is the weight of acetic acid in the sample. The molar ratio of acetic acid to prasugrel hydrobromate in the sample of example 2 is about 1:1, as can be calculated from FIG. 3.
DSC test: Instrument: NETZSCH DSC 204 F1; increasing rate of temperature: 10.0K/min, from 30° C. to 250° C. The results are shown in FIG. 4.

Example 8

Test and Indexing of Acetic Acid Solvated Crystal

Sample: Acetic Acid Solvated Crystal from Example 3 (Crystal A)
X-ray powder diffraction test: Instrument model: Bruker D8 ADVANCE; Light source: Cu-Kα 40 kV 40 mA; graphite monochromator; divergence slit (DS): 1°; anti-scatter slit (SS): 1°; LynxEye array detector, scanning mode: θ/θ, continuous scanning; scanning scope: 3° ~45°, scanning speed: 8°/min. The results are shown in FIG. 5.

Figure 5A:
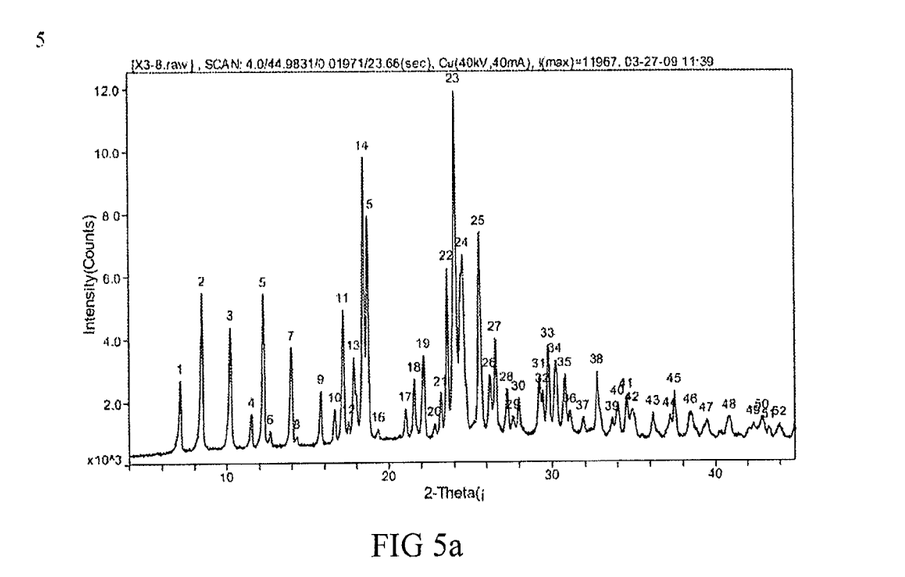
FIG. 5 shows the X-ray powder diffraction pattern of the acetic acid solvated crystal (crystal A) according to example 3.

The peak positions, peak strengths and peak shapes in FIG. 1 match well with those of FIG. 5, and thus the crystals in examples 2 and 3 are the same. The two spectra differ from each other slightly in a few places, which may be caused by experimental errors and crystallinity differences among various batches.

The lattice parameters as obtained by indexing and modifying original powder diffraction spectrogram in example 3 are as follows (the numbers within parentheses are statistical errors):

The crystal is of orthorhombic structure, the space group thereof is Pnma (62). a=15.32642 (0.000202) Å; b=7.38783 (0.00637) Å; c=20.81522 (0.000096) Å; $\alpha=\beta=\gamma=90°$, and the lattice volume thereof=2356.89 Å$^3$.

TABLE 1 comparison table showing peak positions distinguishable in experimental spectrogram, corresponding peak positions as calculated theoretically based on indexing results and deviations

| h | k | l | 2θ (cal) | 2θ (obs) | Delta | I % |
|---|---|---|---|---|---|---|
| 1 | 0 | 1 | 7.157 | 7.136 | 0.021 | 18.8 |
| 0 | 0 | 2 | 8.489 | 8.475 | 0.014 | 41.8 |
| 1 | 0 | 2 | 10.265 | 10.249 | 0.017 | 32.7 |
| 2 | 0 | 0 | 11.538 | 11.513 | 0.025 | 8.6 |
| 2 | 0 | 1 | 12.298 | 12.279 | 0.019 | 42.4 |
| 0 | 1 | 1 | 12.704 | 12.676 | 0.028 | 4.3 |
| 1 | 1 | 1 | 13.959 | 13.976 | -0.017 | 26.9 |
| 2 | 0 | 2 | 14.341 | 14.327 | 0.015 | 2.4 |
| 1 | 1 | 2 | 15.793 | 15.8 | -0.007 | 14.2 |
| 2 | 1 | 0 | 16.654 | 16.65 | 0.004 | 9 |
| 0 | 0 | 4 | 17.025 | 17.036 | -0.011 | 10.5 |
| 2 | 1 | 1 | 17.193 | 17.188 | 0.005 | 35.7 |
| 0 | 1 | 3 | 17.521 | 17.491 | 0.03 | 3.9 |
| 3 | 0 | 1 | 17.863 | 17.857 | 0.006 | 22.1 |
| 1 | 0 | 4 | 17.987 | 17.995 | -0.008 | 11.6 |
| 1 | 1 | 3 | 18.458 | 18.465 | -0.008 | 77.8 |
| 2 | 1 | 2 | 18.72 | 18.706 | 0.015 | 63.5 |
| 3 | 0 | 2 | 19.339 | 19.338 | 0 | 2.3 |
| 2 | 0 | 4 | 20.614 | 20.613 | 0.002 | 0.7 |
| 2 | 1 | 3 | 21.029 | 21.023 | 0.005 | 8.7 |
| 3 | 1 | 1 | 21.557 | 21.553 | 0.003 | 17 |
| 3 | 0 | 3 | 21.583 | 21.589 | -0.006 | 7.8 |
| 1 | 1 | 4 | 21.661 | 21.658 | 0.003 | 5.2 |
| 1 | 0 | 5 | 22.108 | 22.099 | 0.009 | 22.1 |
| 3 | 1 | 2 | 22.804 | 22.805 | -0.001 | 4.2 |
| 4 | 0 | 0 | 23.195 | 23.196 | -0.001 | 13.2 |
| 4 | 0 | 1 | 23.59 | 23.576 | 0.014 | 49.9 |
| 2 | 1 | 4 | 23.903 | 23.909 | -0.005 | 43.7 |
| 0 | 2 | 0 | 24.072 | 24.066 | 0.006 | 100 |
| 2 | 0 | 5 | 24.311 | 24.313 | -0.002 | 36.7 |
| 3 | 0 | 4 | 24.396 | 24.423 | -0.027 | 43.7 |
| 0 | 1 | 5 | 24.524 | 24.54 | -0.016 | 49.3 |
| 4 | 0 | 2 | 24.74 | 24.735 | 0.005 | 12.4 |
| 1 | 2 | 1 | 25.144 | 25.141 | 0.003 | 1.5 |
| 1 | 1 | 5 | 25.212 | 25.207 | 0.005 | 1.5 |
| 0 | 2 | 2 | 25.567 | 25.566 | 0.002 | 59.5 |
| 0 | 0 | 6 | 25.657 | 25.653 | 0.004 | 46.1 |
| 4 | 1 | 0 | 26.178 | 26.179 | -0.002 | 16.6 |
| 1 | 2 | 2 | 26.23 | 26.212 | 0.018 | 14.4 |
| 1 | 0 | 6 | 26.318 | 26.308 | 0.01 | 10 |
| 4 | 1 | 1 | 26.531 | 26.536 | -0.005 | 26.3 |
| 4 | 0 | 3 | 26.553 | 26.551 | 0.002 | 28.5 |
| 2 | 2 | 0 | 26.769 | 26.763 | 0.007 | 1.7 |
| 2 | 2 | 1 | 27.116 | 27.114 | 0.002 | 2.5 |
| 2 | 1 | 5 | 27.179 | 27.183 | -0.004 | 9 |
| 3 | 1 | 4 | 27.256 | 27.261 | -0.005 | 13.1 |
| 4 | 1 | 2 | 27.567 | 27.572 | -0.005 | 4.2 |
| 3 | 0 | 5 | 27.617 | 27.621 | -0.004 | 5.3 |
| 1 | 2 | 3 | 27.953 | 27.954 | -0.001 | 11.1 |
| 2 | 2 | 2 | 28.131 | 28.124 | 0.007 | 1.7 |
| 2 | 0 | 6 | 28.213 | 28.209 | 0.004 | 1.9 |
| 1 | 1 | 6 | 29.001 | 28.996 | 0.005 | 2.2 |
| 4 | 1 | 3 | 29.217 | 29.215 | 1.00E-03 | 17.6 |
| 5 | 0 | 1 | 29.429 | 29.427 | 1.00E-03 | 13.1 |
| 0 | 2 | 4 | 29.633 | 29.631 | 0.002 | 10.8 |

TABLE 1-continued comparison table showing peak positions distinguishable in experimental spectrogram, corresponding peak positions as calculated theoretically based on indexing results and deviations

| h | k | l | 2θ (cal) | 2θ (obs) | Delta | I % |
|---|---|---|---|---|---|---|
| 2 | 2 | 3 | 29.753 | 29.763 | -0.011 | 27.7 |
| 3 | 2 | 1 | 30.137 | 30.133 | 0.004 | 13.2 |
| 3 | 1 | 5 | 30.195 | 30.181 | 0.013 | 16.8 |
| 1 | 2 | 4 | 30.213 | 30.216 | -0.003 | 19.4 |
| 5 | 0 | 2 | 30.373 | 30.37 | 0.003 | 4 |
| 1 | 0 | 7 | 30.6 | 30.609 | -0.009 | 7 |
| 2 | 1 | 6 | 30.745 | 30.769 | -0.024 | 16.7 |
| 3 | 2 | 2 | 31.062 | 31.064 | -0.002 | 6.9 |
| 4 | 0 | 5 | 31.712 | 31.717 | -0.005 | 1 |
| 5 | 1 | 1 | 31.873 | 31.874 | -0.002 | 4.9 |
| 2 | 2 | 4 | 31.896 | 31.903 | -0.006 | 4.5 |
| 2 | 0 | 7 | 32.265 | 32.263 | 0.002 | 1.5 |
| 5 | 1 | 2 | 32.753 | 32.76 | -0.006 | 19.8 |
| 1 | 2 | 5 | 32.912 | 32.922 | -0.01 | 6.6 |
| 3 | 1 | 6 | 33.468 | 33.474 | -0.006 | 1.2 |
| 4 | 2 | 0 | 33.674 | 33.671 | 0.003 | 5.4 |
| 5 | 0 | 4 | 33.913 | 33.906 | 0.007 | 6.8 |
| 4 | 2 | 1 | 33.956 | 33.956 | 1.00E-03 | 7.7 |
| 4 | 1 | 5 | 34.008 | 34.023 | -0.015 | 9.9 |
| 5 | 1 | 3 | 34.176 | 34.171 | 0.005 | 2.1 |
| 2 | 2 | 5 | 34.477 | 34.465 | 0.011 | 8.1 |
| 3 | 2 | 4 | 34.538 | 34.571 | -0.033 | 11.5 |
| 4 | 0 | 6 | 34.858 | 34.871 | -0.013 | 8 |
| 1 | 0 | 8 | 34.949 | 34.928 | 0.021 | 7.5 |
| 6 | 0 | 0 | 35.101 | 35.093 | 0.009 | 5.6 |
| 1 | 2 | 6 | 35.964 | 35.971 | -0.007 | 1.1 |
| 5 | 1 | 4 | 36.085 | 36.101 | -0.016 | 4.3 |
| 6 | 0 | 2 | 36.179 | 36.187 | -0.008 | 6.9 |
| 5 | 0 | 5 | 36.367 | 36.373 | -0.006 | 1.3 |
| 2 | 0 | 8 | 36.437 | 36.44 | -0.003 | 1.1 |
| 3 | 2 | 5 | 36.956 | 36.964 | -0.008 | 2.6 |
| 1 | 1 | 8 | 37.068 | 37.062 | 0.006 | 2.4 |
| 1 | 3 | 1 | 37.2 | 37.199 | 1.00E-03 | 6.6 |
| 6 | 0 | 3 | 37.488 | 37.488 | -0.001 | 14.6 |
| 4 | 0 | 7 | 38.282 | 38.273 | 0.01 | 4.4 |
| 5 | 2 | 1 | 38.372 | 38.38 | -0.008 | 7.6 |
| 2 | 1 | 8 | 38.485 | 38.478 | 0.008 | 5.9 |
| 2 | 3 | 1 | 38.613 | 38.611 | 0.002 | 6.2 |
| 3 | 0 | 8 | 38.808 | 38.828 | -0.02 | 2.3 |
| 6 | 0 | 4 | 39.257 | 39.248 | 0.009 | 3 |
| 6 | 1 | 3 | 39.489 | 39.465 | 0.025 | 5.2 |
| 4 | 1 | 7 | 40.25 | 40.23 | 0.02 | 1.6 |
| 0 | 1 | 9 | 40.851 | 40.842 | 0.009 | 5.7 |
| 6 | 0 | 5 | 41.439 | 41.443 | -0.005 | 1.2 |
| 7 | 0 | 2 | 42.14 | 42.124 | 0.016 | 2.6 |
| 5 | 0 | 7 | 42.311 | 42.36 | -0.049 | 4.4 |
| 3 | 2 | 7 | 42.831 | 42.855 | -0.024 | 5.8 |
| 7 | 0 | 3 | 43.297 | 43.305 | -0.009 | 4.1 |
| 4 | 3 | 1 | 43.883 | 43.879 | 0.004 | 3.1 |

The results of relevant parameters in the indexing are as follows:

angle error $|\delta 2\theta|=0.0058°$; zero offset=0.0°; quality factor F(30)=45.3(110).

Based on the less angle error, no zero offset, and the well matched experimental and theoretical spectrum line position, the indexing results are reliable.

The results indicate that the sample as provided is a pure phase compound and the corresponding experimental spectrogram can be used as data and finger-print for distinguishing the same phase.

Example 9

Test and Indexing of Non-Solvated Crystal

Sample: Non-Solvated Crystal from Example 6 (Crystal B)
X-ray powder diffraction test: Instrument model: Bruker D8 ADVANCE; Light source: Cu-Kα 40 kV 40 mA; graphite monochromator; divergence slit (DS): 1°; anti-scatter slit (SS): 1°; LynxEye array detector, scanning mode: θ/θ, continuous scanning; scanning scope: 3° ~45°, scanning speed: 8°/min. The results are shown in FIG. 6.

Figure 6A:
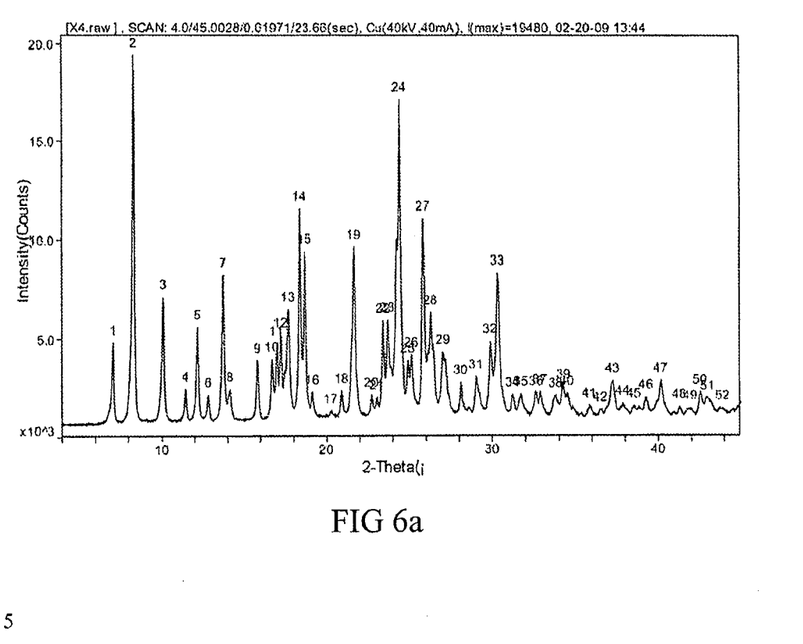
FIG. 6 shows the X-ray powder diffraction pattern of the crystal (crystal B) according to example 6.
Figure 7:
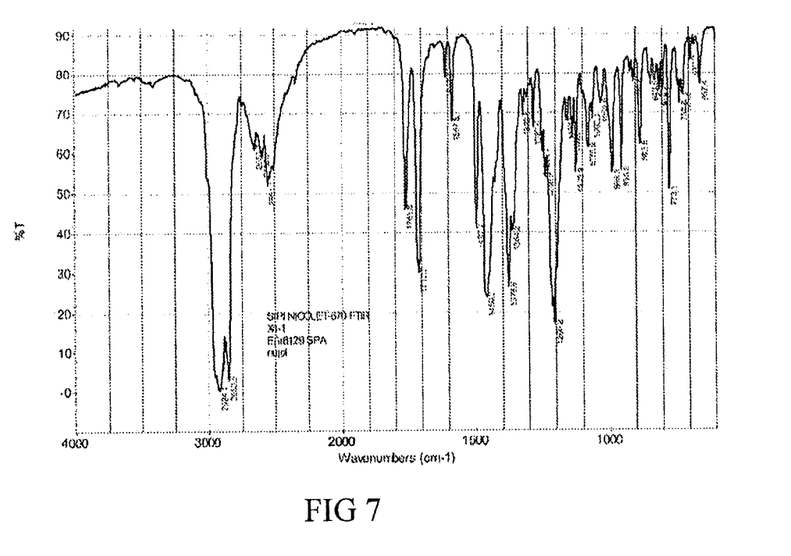
FIG. 7 shows the infrared absorption spectrum of the crystal (crystal B) according to example 6.

There are significant differences in peak positions, peak strengths and peak shapes between FIGS. 1 and 6, and thus the crystals in examples 6 and 2 are different.

The lattice parameters as obtained by indexing and modifying the original powder diffraction spectrogram in example 6 are as follows:

The crystal is of orthorhombic structure, the space group thereof is Pnma (62). a=15.42456 Å; b=7.28661 Å; c=21.23884 Å; α=β=γ=90°, and the lattice volume=2387.09 Å$^3$. Quality factor F(30)=25.4(117).

With respect to crystals A and B: (1) the molecule of crystal B is one acetic acid molecule less than that of crystal A, the molecular weight is thus less; however, the lattice volume of crystal B is larger than that of crystal A, as hydrogen bond is formed between the acetic acid molecule and prasugrel molecule, which results in more compact and ordered space structure of crystal A. In the stability test, the stability of crystal A is better than crystal B. The difference in stability is due to the difference in space structure.

Example 10

Influence Factor Test

Sample Sources:
X1 (crystal of prasugrel hydrochlorate) was prepared according to the method provided in example 1 of CN1452624A
X2 (prasugrel hydrobromate) was prepared according to the method provided in example 1 of CN101255169A
X3 (acetic acid solvate of prasugrel hydrobromate) was prepared according to the method in example 2 of the present invention Experimental method: refer to Pharmacopoeia of the People's Republic of China. 2005 ed. Part 2. Appendix XIX C
HPLC conditions: instrument: Agilent 1100
Chromatographic column: Phenomenex Hyperclone 5μ BDS C18
Mobile phase: acetonitrile: $KH_2PO_4$ (10 mM)=70:30
Column temperature: 40° C.
Flow rate: 1.0 ml/min
Wavelength: 220 nm
Experimental results:

TABLE 2

| Experimental conditions | Samples | Purity (HPLC area normalization) $t_R$ 6.2 |
| --- | --- | --- |
| 0 day | X1 | 99.08 |
|  | X2 | 99.83 |
|  | X3 | 99.84 |
| 60° C. for 5 days | X1 | 98.89 |
|  | X2 | 99.39 |
|  | X3 | 99.72 |
| 60° C. for 10 days | X1 | 98.29 |
|  | X2 | 99.01 |
|  | X3 | 99.46 |
| light for 5 days | X1 | 98.49 |
|  | X2 | 99.40 |
|  | X3 | 99.56 |
| light for 10 days | X1 | 98.20 |
|  | X2 | 98.83 |
|  | X3 | 99.57 |
| RH 92.5% 5 days | X1 | 98.39 |
|  | X2 | 96.62 |

TABLE 2-continued

| Experimental conditions | Samples | Purity (HPLC area normalization) $t_R$ 6.2 |
| --- | --- | --- |
|  | X3 | 99.65 |
| RH 92.5% 10 days | X1 | 98.20 |
|  | X2 | 96.12 |
|  | X3 | 99.50 |

Table 2 shows the stability analysis results of acetic acid solvate in example 2. The stability test results show that under all the conditions of light, 60° C., and RH 92.5%, the acetic acid solvate of prasugrel hydrobromate (X3) is more stable than the hydrochlorate crystal (X1) and the prasugrel hydrobromate (X2).

Example 11

Solubility of Acetic Acid Solvate

Sample Sources: the Same as Example 10
Experimental method: refer to Pharmacopoeia of the People's Republic of China. 2005 ed. Part 2. General Notices.
Experimental Results:

TABLE 3

| Substances | Solubility (0.1N hydrogen chloride aqueous solution) | |
| --- | --- | --- |
| X1 | slightly soluble | 1 g/44 ml |
| X2 | degraded | 1 g/17 ml |
| X3 | easily soluble | 1 g/7 ml |

Obviously, acetic acid solvated crystal of prasugrel hydrobromate has better solubility than prasugrel hydrobromate and hydrochlorate.

The invention claimed is:
1. A crystal of a compound having formula II:

II wherein:
Sol is acetic acid; and
m is 1.
2. The crystal of claim 1, wherein in an X-ray powder diffraction pattern of the crystal measured with Cu-Kα radiation, diffraction peaks expressed as interplanar spacing d are found at about 10.43 Å, 8.63 Å, 7.20 Å, 6.33 Å, 5.15 Å, and 3.47 Å.
3. The crystal of claim 2, wherein in the X-ray powder diffraction pattern of the crystal measured with Cu-Kα radiation, diffraction peaks expressed as interplanar spacing d are found at about 10.43 Å, 8.63 Å, 7.20 Å, 6.33 Å, 5.15 Å, 4.80 Å, 4.73 Å, 3.77 Å, 3.68 Å, and 3.47 Å.
4. The crystal of claim 3, wherein in the X-ray powder diffraction pattern of the crystal measured with Cu-Kα radiation, diffraction peaks expressed as interplanar spacing d are found at about 12.38 Å, 10.43 Å, 8.63 Å, 7.20 Å, 6.33 Å, 5.15 Å, 4.96 Å, 4.80 Å, 4.73 Å, 4.02 Å, 3.77 Å, 3.68 Å, 3.47 Å, 3.36 Å, 2.99 Å, and 2.95 Å.

5. The crystal of claim 1, wherein the crystal is of orthorhombic structure, and the space group thereof is Pnma; the lattice parameters thereof approximately are: a=15.33 Å; b=7.39 Å; c=20.82 Å; α=β=γ=90'; and the lattice volume thereof is 2356.89 Å$^3$.

6. A pharmaceutical composition comprising a therapeutically effect amount of a crystal of a compound having formula II:

II wherein:
Sol is acetic acid; and
m is 1.

7. A method for preventing diseases associated with thrombus in an animal, comprising administering to the animal in need thereof a therapeutically effective amount of a crystal of a compound having formula II:

II wherein:
Sol is acetic acid, and
m is 1.

8. A crystal composition comprising the crystal of claim 1 in an amount of 60% or more by weight.

9. The crystal composition of claim 8, comprising the crystal of claim 1 in an amount of 90% or more by weight.

10. The crystal composition of claim 8, comprising the crystal of claim 1 in an amount of 95% or more by weight.

11. The crystal composition of claim 8, comprising the crystal of claim 1 in an amount of 99% or more by weight.

* * * * *